United States Patent
Masaoka et al.

(10) Patent No.: US 6,299,600 B1
(45) Date of Patent: Oct. 9, 2001

(54) LIQUID PUMP

(75) Inventors: Katsunori Masaoka; Atsushi Ikeda, both of Hiroshima; Teruhisa Saitoh, Saitama, all of (JP)

(73) Assignee: JMS Co., Ltd. (JP)

( * ) Notice: Subject to any disclaimer, the term of this patent is extended or adjusted under 35 U.S.C. 154(b) by 0 days.

(21) Appl. No.: 09/743,031

(22) PCT Filed: Jun. 29, 2000

(86) PCT No.: PCT/JP99/03558
 § 371 Date: Jan. 2, 2001
 § 102(e) Date: Jan. 2, 2001

(87) PCT Pub. No.: WO00/01433
 PCT Pub. Date: Jan. 13, 2000

(30) Foreign Application Priority Data

Jul. 2, 1998 (JP) ................................................. 10-187833
 Feb. 3, 1999 (JP) ................................................. 11-026086

(51) Int. Cl.⁷ .................................................. A61M 1/00
(52) U.S. Cl. ........................................... 604/118; 604/151
(58) Field of Search ..................................... 604/131, 151, 604/153, 30, 34, 503, 118–120; 417/474–477

(56) References Cited

U.S. PATENT DOCUMENTS 5,395,320 * 3/1995 Padda et al. ............................ 604/65
5,683,367 * 11/1997 Jordan et al. ......................... 604/118
5,695,464 * 12/1997 Viallet .................................... 604/67
5,791,880 * 8/1998 Wilson ................................... 417/14
5,904,668 * 5/1999 Hyman et al. ....................... 604/131

FOREIGN PATENT DOCUMENTS

| 62-291516 A | 12/1987 | (JP) . |
| 4-64107 A | 2/1992 | (JP) . |
| 7-210249 A | 8/1995 | (JP) . |
| 7-114810 B2 | 12/1995 | (JP) . |

* cited by examiner

Primary Examiner—Sharon Kennedy
(74) Attorney, Agent, or Firm—Baker & Daniels

(57) ABSTRACT

When the control unit feedback-controls the DC brushless motor of the roller pump 5 to be driven for transferring the liquid in the flexible tube by using the pulse number of the encoder pulse from the encoder unit, the pulse number of the 4-multiplied encoder pulse, which is obtained by multiplying the pulse number of the encoder pulse by 4 by means of the frequency 4-multiplying circuit, is counted by means of the pulse counter. Therefore, since the encoder unit can multiply the pulse number of the encoder pulse which corresponds to the rotation of the output shaft of the DC brushless motor, the liquid in the flexible tube can be transferred with high constantivity even if the light-passing portion and the light-interrupting portion of the first and second encoding patterns can not been increased due to structural limitation. That is, since the resolution of the liquid flow rate to be detected with the encoder pulse to be output by the encoder unit is enhanced, the number of rotation of the output shaft of the DC brushless motor can be detected with sufficiently high resolution even if the rotation speed of the output shaft of the DC brushless motor are lowered 9 Claims, 8 Drawing Sheets

LIQUID PUMP

TECHNICAL FIELD

The present invention relates to a liquid transferring pump system to be used for transferring a liquid such as liquid medicine or blood, wherein a flexible tube, in which the liquid flows, is squeezed with a movable squeezing member such as a roller and the movable squeezing member is moved by means of a motor so as to constant-flow-transfer the liquid in the tube.

BACKGROUND ART

A roller pump is conventionally known as one of drivers of constant-flowtransferring of a liquid in a flexible tube.

In this roller pump, free rollers stands at uniform intervals on a periphery portion of a disc to be rotated by a motor, which free rollers are supported by respective pivots. Outside surfaces of the free rollers protrude over the disc, and a supporting member is arranged oppositely to the free rollers. The flexible tube is put between the free rollers and the supporting member, and the disc is rotated so that the liquid in the flexible tube can be constant-flow-transferred according to the rotation speed of the disc.

In the field of medicine for example, the above roller pump is used for the artificial dialyzer for circulating the blood, especially when a relatively large quantity of liquid is constant-flow-transferred. When a relatively small quantity of liquid is constant-flow-transferred as in case of dosing liquid medicine by means of an intravenous injection, a drip tube provided between an injection needle and a liquid medicine bag is generally used.

In this way, the reason for using the roller pump for constant-flow-transferring a relatively large quantity of liquid is to carry out the feedback control necessary for securely carrying out the constant-flow-transferring, not because of the limitation of function of a motor.

More specifically, flow fluctuation could generally occur during the constant-flow-transferring of the liquid. When flow fluctuation degree is the same, the larger the flow rate is, the smaller the flow fluctuation rate is. That is, the degree of losing the transferring constantivity is larger when a relatively small quantity of liquid is transferred.

Accordingly, when the motor is continuously rotated with low speed in order to constant-flow-transfer a relatively small quantity of liquid, the motor rotation must be monitored in a shorter period in executing the feedback control, which requires a device to accurately detect the motor rotation number.

However, an encoder, which is used to detect the motor rotation, has structurally a limitation of upper frequency of pulse to be output according to the motor rotation number. Therefore, when the motor rotation speed is too low, the motor rotation number can not be detected with a required high resolution corresponding to the transferring rate when the relatively small quantity of liquid is constant-flow-transferred.

Based on such a background, in the field of medicine, a drip tube has been conventionally used for the small constant-rate dosing of liquid medicine. And, in case that it is difficult to use the drip tube since the dosing amount is too much to use a liquid medicine bag, the roller pump is operated by intermittently driving the motor.

However, though the above operation of the roller pump could keep the above small transferring in a long span of time, the liquid transferring completely stops in a short span of time since the motor intermittently stops. Some liquids or substances to be transferred, however, could not allow such an intermittent transferring. Or, the above intermittent operation could make an operator misunderstand that failure arose, which requires a means to show the intermittent operation.

DISCLOSURE OF THE INVENTION

In view of the foregoing, an object of the present invention is provide a liquid transferring pump system such as a roller pump for constant-flow-transferring a liquid in a flexible tube from the upstream side to the downstream side by squeezing the tube by a movable squeezing member to be moved along the tube, wherein the transferring constantivity can be kept high even if the transferring rate (per unit time) of the liquid is relatively small.

And, in order to achieve the above object, the liquid transferring pump system of the present invention as set forth in claim 1, wherein a motor for moving a movable squeezing member, which squeezes a flexible tube so as to transfer a liquid therein from an upstream side toward an downstream side thereof, is driven according to a drive pulse signal having a frequency determined correspondingly to a target flow rate of the liquid in the tube, and the frequency of the drive pulse signal is increased and decreased according to the frequency determined correspondingly to the target flow rate on a basis of the frequency of the drive pulse signal and a frequency of a rotation pulse signal which is output by an encoder correspondingly to rotation number of the motor so that a flow rate of the liquid in the tube agrees with the target flow rate, and wherein comprising a frequency multiplying means to receive the rotation pulse signal to be output by the encoder and then to output a multiplied pulse signal to be obtained by multiplying the frequency of the rotation pulse signal by n and a drive frequency adjusting means to increase and decrease the frequency of the drive pulse signal according to the frequency determined correspondingly to the target flow rate so that a frequency of the multiplied pulse signal converges in the frequency determined correspondingly to the target flow rate are provided, is characterized in that the drive frequency adjusting means has a desirable drive pulse calculating means to calculate pulse number, per unit time, of an ideal drive pulse signal for converging the frequency of the multiplied pulse signal in the frequency determined correspondingly to the target flow rate at every determined time period when the frequency of the multiplied pulse signal is calculated based on sampling number of the multiplied pulse signal, an integer judging means to judge whether or not the pulse number, per the unit time, of the ideal drive pulse signal is integer, an approximate pulse calculating means to calculate a first approximate pulse number and a second approximate pulse number, which are two integers smaller and larger, respectively, than the pulse number, per the unit time, of the ideal drive pulse signal, when the integer judging means has judged that the pulse number, per the unit time, of the ideal drive pulse signal is not integer, and a period calculating means to calculate the first period time and the second period time wherein a total of a first value of multiplying the first approximate pulse number by the first period time and a second value of multiplying the second approximate pulse number by the second period time is equal to a value of multiplying the pulse number, per the unit time, of the ideal drive pulse signal by the unit time and also another total of the first period time and the second period time is equal to the unit time, wherein, when the integer judging means has judged that the pulse number, per the unit time, ofthe ideal drive pulse signal is not integer, increase and decrease of the frequency of the drive pulse signal according to the frequency determined correspondingly to the target flow rate is carried out by means of successively executing a pulse signal output of the first approximate pulse number over the first period time and a pulse signal output of the second approximate pulse number over the second period time.

BEST MODE OF THE INVENTION

Specific Structure of Liquid Transferring Pump System in Accordance with Preferred Embodiment of the Present Invention First, a reference embodiment of the present invention is described with reference to FIGS. 1 to 5 before describing the structure of the liquid transferring pump system in accordance with the embodiment of the present invention.

Figure 1:
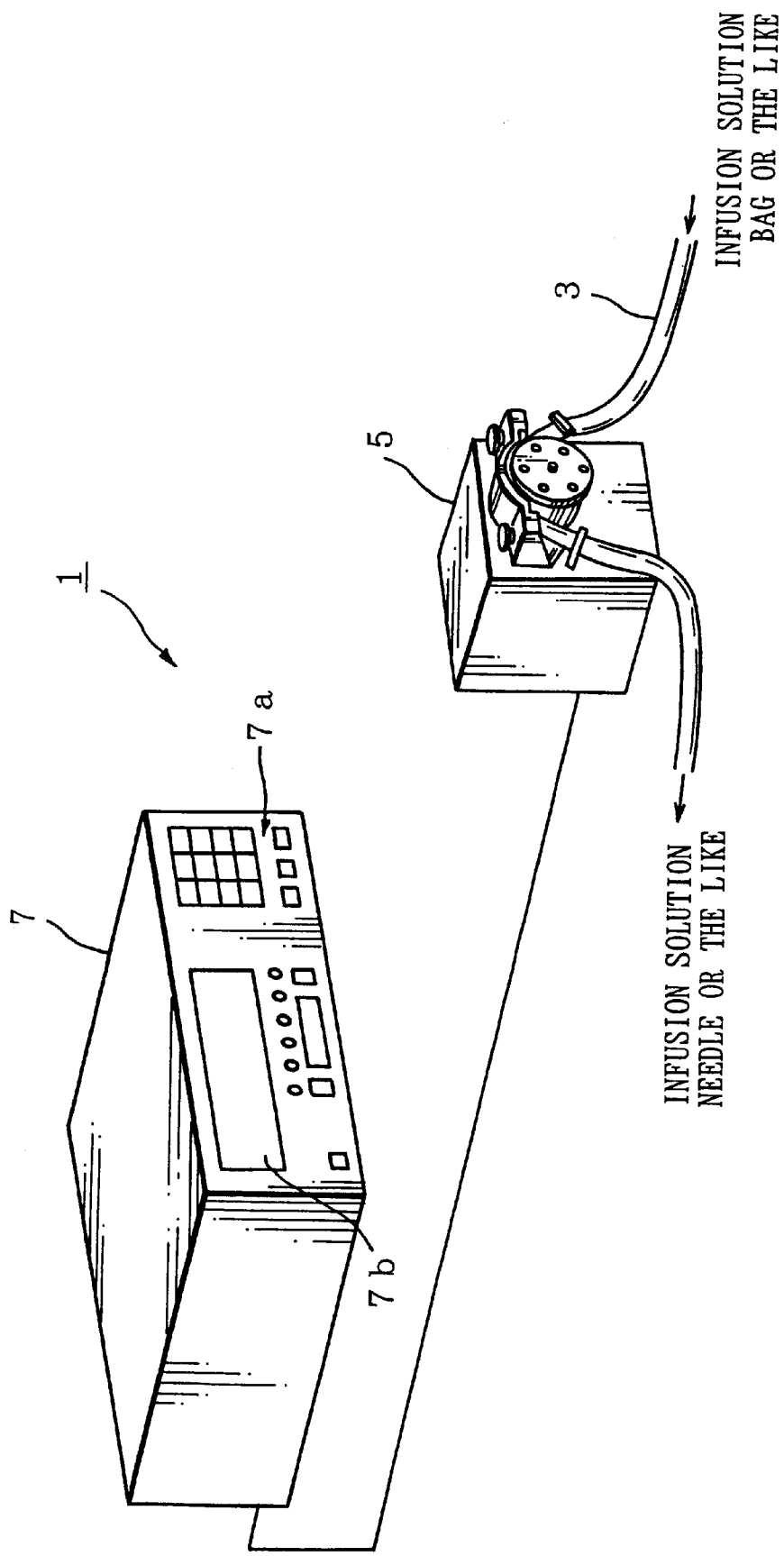
FIG. 1 is an outline structure of a liquid transferring pump system in accordance with a reference embodiment of the present invention.

FIG. 1 is an outline structure of the liquid transferring pump system in accordance with the reference embodiment of the present invention. The liquid transferring pump system is designated with reference character 1 in FIG. 1. The liquid transferring pump system 1 is used to constant-flow-transfer a liquid (not illustrated) to flow in a flexible tube 3 (tube) from an infusion solution bag (not illustrated) connected to one end of the flexible tube 3 toward an infusion solution needle (not illustrated) connected to the other end of the flexible tube 3.

And, the liquid transferring pump system 1 has a roller pump 5 and a controller 7 to control drive of the roller pump 5.

Figure 2:
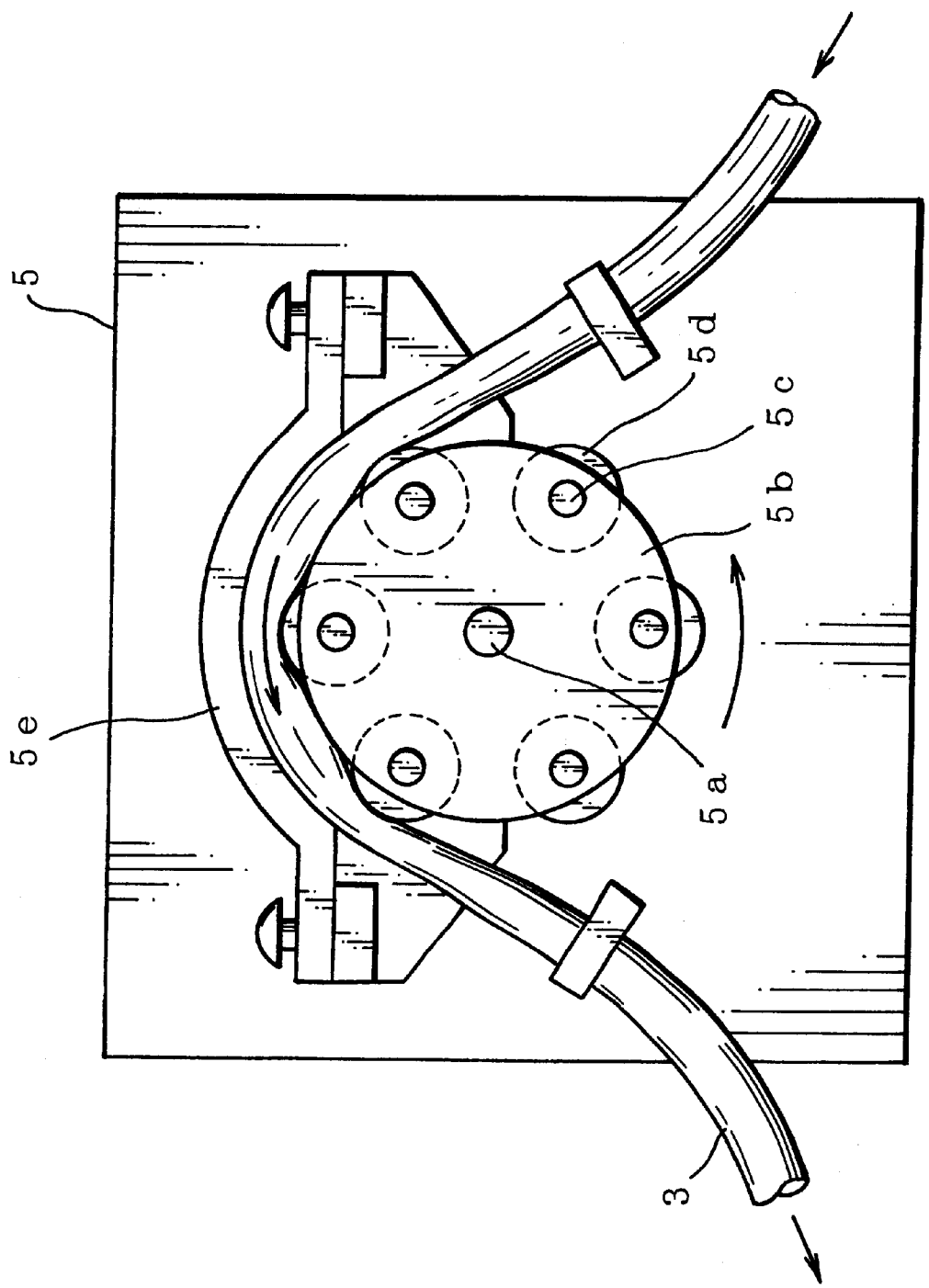
FIG. 2 is an enlarged front view of a roller pump shown in FIG. 1.

As is shown in FIG. 2, the above roller pump 5 has a disc 5b connected to the end of a driving shaft 5a to be rotated by a motor unit 50 (FIG. 3) built in the roller pump 5. A pivot 5c stands on a plurality of periphery portions of the disc 5b at regular intervals in a circumferential direction of the disc 5b, and a free roller 5d (movable squeezing member) is pivotally supported with each of the pivots 5c in a state that the circumferential surface of each of the free rollers 5d outwardly protrudes a little from the disc 5b. And, a supporting plate 5e concentrically arranged with the disc 5b faces the circumferential surfaces of the free rollers Sd along the free rollers 5d.

The roller pump 5 with the above structure is used in a state that the flexible tube 3 is put between the circumferential surfaces of the free rollers 5d of the disc 5b and an inside surface of the supporting plate 5e.

Similarly to the conventional one, the disc 5b is rotated by a DC brushless motor 51 so that liquid inside a part of the flexible tube 3 between two free rollers 5d facing the supporting plate 5e flows from the upstream side to the downstream side. in a rotatory direction of the disc 5b, whereby liquid in the flexible tube 3 constant-flow-transfers from one end side of the flexible tube 3 to the other end side according to the rotation speed of the disc 5b.

Figure 3:
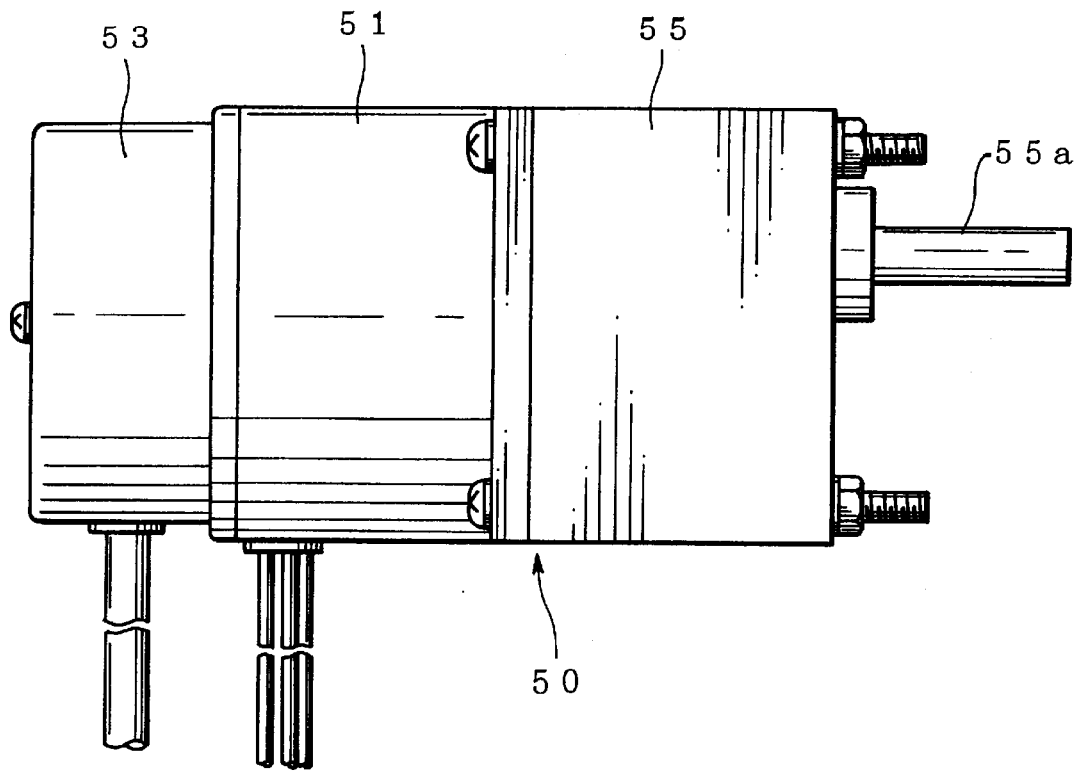
FIG. 3 is a side view of a motor unit being built in the roller pump of FIG. 2.

As shown I FIG. 3, the above motor unit 50 is connected with an encoder unit 53 at one output shaft (not illustrated) of the DC brushless motor 51 (motor) and with a gear head 55 having a reduction gear train at the other output shaft (not illustrated).

A reduction output shaft 55a directly connected with the above driving shaft 5a is protrusively-provided on the gear head 55.

Figure 4:
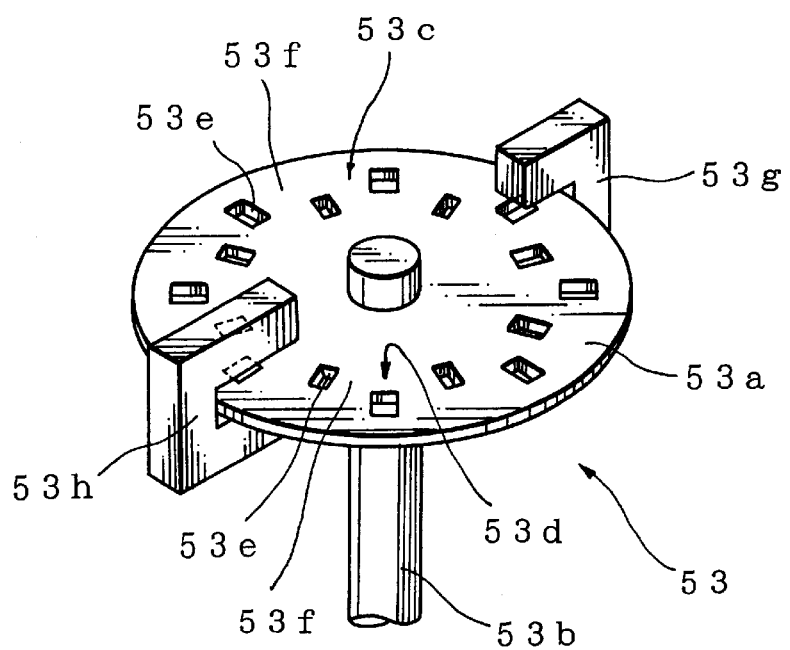
FIG. 4 is a perspective view schematically showing an encoder unit shown in FIG. 3.

And, as shown in FIG. 4, the encoder unit 53 has both of a circular-tabular base plate 53a, on which first encoding patterns 53c and second encoding patterns 53d are concentrically arranged, and first and second photointerrupters 53g,53h which optically read the first and second encoding patterns 53c,53d, respectively, and convert them into electric signals. A central shaft 53b of the base plate 53a is connected to a non-illustrated output shaft of the DC brushless motor 51.

The first and second encoding patterns 53c,53d each consist of light-passing portions 53e, i.e. slits, which are arranged at regular intervals of angle in a circumferential direction of the base plate 53a, and light-interrupting portions 53f each of which is of a part of the base plate 53a arranged between the two adjacent light-passing portions 53e.

The first and second photo-interrupters 53g,53h each have a light emitting element and a light receiving element (not illustrated) which are oppositely arranged on the respective front and back sides, or viceversa, of the base plate 53a.

Specifically, the first photo-interrupter 53g is arranged so that the first encoding pattern 53c is put between the light emitting element and the light receiving element, and the light-passing portion 53e comes between the light emitting and receiving elements and next the light-interrupting portion 53f comes between them when the base plate 53a rotates.

And, the light receiving element of the first photo-interrupter 53g detects the detection light from the light emitting element when the light-passing portion 53e is positioned therebetween and does not detect the detection light when the lightinterrupting portion 53f is positioned therebetween. Consequently, the first photo-interrupter 53g generates the determined number of first encoder pulses (i.e. subrotation pulse signal) during one rotation of the output shaft of the DC brushless motor 51 (i.e. in the reference embodiment, 250 pulses/rotation).

On the other hand, the second photo-interrupter 53h is arranged so that the second encoding pattern 53d is put between the light emitting element and the light receiving element, and the light-passing portion 53e comes between the light emitting and receiving elements and next the light-interrupting portion 53f comes between them when the base plate 53a rotates.

And, the light receiving element of the second photo-interrupter 53h detects the detection light from the light emitting element when the light-passing portion 53e is positioned therebetween and does not detect the detection light when the lightinterrupting portion 53f is positioned therebetween. Consequently, the second photo-interrupter 53h generates the same number of second encoder pulses (i.e. subrotation pulse signal) as that of first encoder pulse during one rotation of the output shaft of the DC brushless motor 51 (i.e. in the reference embodiment, 250 pulses/rotation), which second encoder pulse has a phase difference of half the pulse period of the first encoder pulse.

The encoder unit 53 formed above generates twice the above determined number of encoder pulses since the first and second encoder pulses are added (i.e. in the reference embodiment, 500 pulses/rotation) during one rotation of the output shaft of the DC brushless motor 51, which encoder pulse corresponds to the m-multiplied pulse signal in claim 3 to be obtained by multiplying the determined frequency by m, namely to the rotation pulse signal in claim 1 to be output by the encoder.

As described above, the first phase encoder corresponding to the sub-encoder in the claim can be forned by the first encoding pattern 53c and the first photo-interrupter 53g in this reference embodiment, and similarly the second phase encoder corresponding to the sub-encoder in the claim can be formed by the second encoding pattern 53d and the second photo-interrupter 53h in this reference embodiment.

The above gear head 55 (a reduction mechanism) reduces rotation of the output shaft of the DC brushless motor 51 by means of an internal reduction gear train, i.e. one-60th in case of the reference embodiment, and outputs to the reduction output shaft 55a connected to the driving shaft 5a of the roller pump 5.

As shown in FIG. 1, the above controller 7 has, on the front, such as a basic data setting-inputting portion 7a consisting of ten-keys and the like and an indicating portion 7b to be of the liquid-crystal display on which basic data having been input-set by the basic data setting-inputting portion 7a and an operating state of the roller pump 5 are indicated.

An inside diameter of the flexible tube 3, a basic flow rate of the liquid in the flexible tube 3, operation time of the roller pump 5, and the like are input-set from the basic data setting-inputting portion 7a.

And the input-setting of the basic data by the basic data setting-inputting portion 7a, various indication by the indicating portion 7b, and the driving of the roller pump 5 based on the encoder pulse from the encoder unit 53 and on the basic data from the basic data setting-inputting portion 7a are controlled by means of the control unit which can be composed of an analogue or digital circuit and the microcomputer to execute a determined program.

Figure 5:
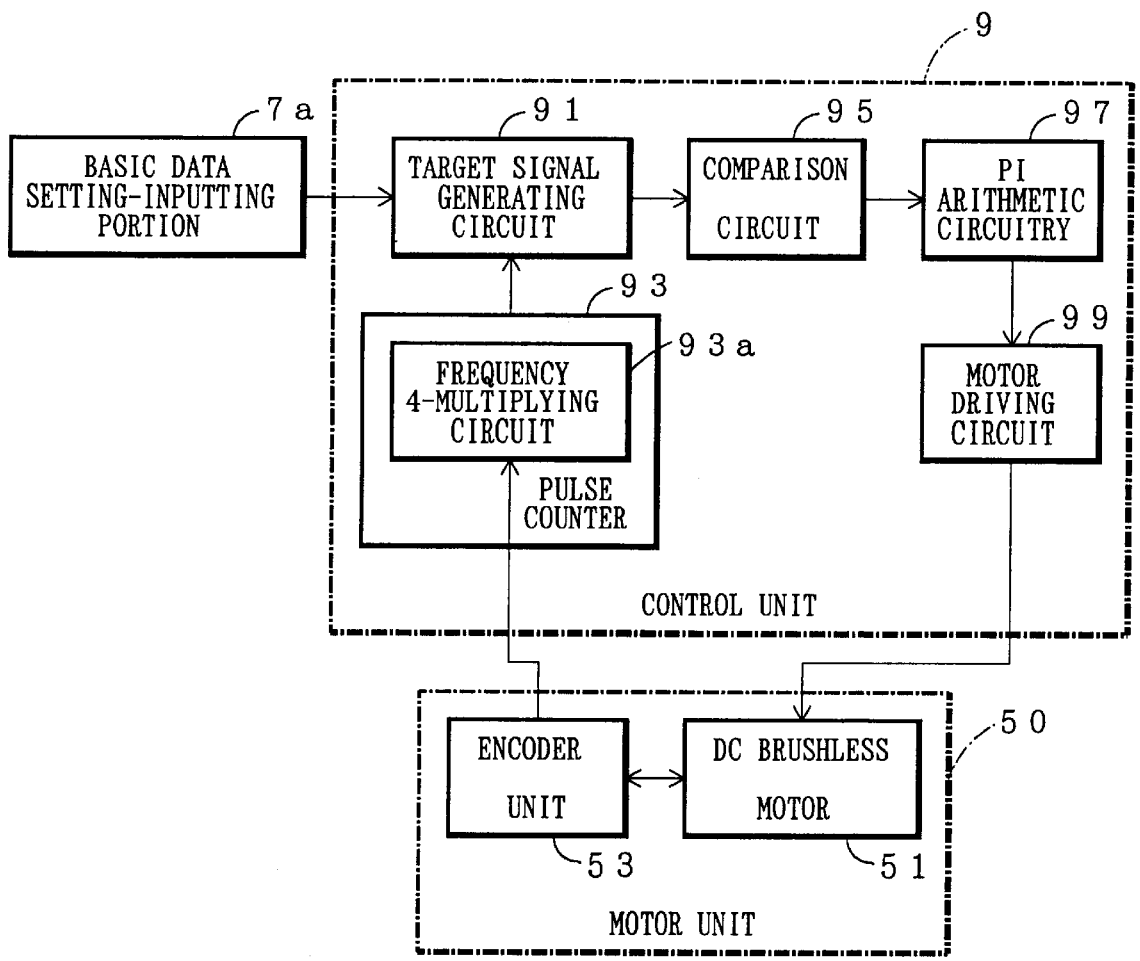
FIG. 5 is a block diagram showing an electrical structure of a control unit to control the drive of the roller pump of FIG. 2 in a reference embodiment of the liquid transferring pump system in accordance with the present invention.

Next, the control unit of the liquid transferring pump system in accordance with the reference embodiment of the present invention is described referring to a block diagram of FIG. 5.

The control unit 9 of the liquid transferring pump system of the reference embodiment is made up of an analogue or digital circuit, while having a target signal generating circuit 91, a pulse counter 93, a comparison circuit 95, and a PI arithmetic circuitry 97 and a motor driving circuit 99.

The above target signal generating circuit 91 generates a target signal to give a target value of rotation of the output shaft of the DC brushless motor 51 on the basis the inside diameter of the flexible tube 3 and the basic flow rate having been input/set as the basic data by means of the basic data setting-inputting portion 7a.

The above pulse counter 93 is a circuit to count the number of the encoder pulse to be output from the encoder unit 53. Specifically, the pulse counter 93 counts the number of a 4-multiplied encoder pulse to be formed by being multiplied by four (4) by dividing one encoder pulse into four (4) pulses each having one-fourth period of the encoder pulse by means of a frequency 4-multiplying circuit 93a (a frequency multiplying means) to be formed by, for example, multivibrator circuits or the like to be built in the pulse counter 93. The 4-multiplied encoder pulse corresponds to a m*n-multiplied pulse signal to be got by multiplying the determined frequency in claim 3 by "m×n" and, that is, corresponds to a multiplied pulse signal to be got by multiplying the frequency of a rotation pulse signal in claim 1 by "n".

Accordingly, for example, based on the first encoder pulse to be output by the first phase encoder of the encoder unit 53, at first, the frequency of the first encoder pulse is multiplied by 2 by being composed with the second encoder pulse to be output by the second phase encoder at the encoder unit 53 and further multiplied by 4 by the frequency 4-multiplying circuit 93a of the pulse counter 93, whereby the frequency of the first encoder pulse is multiplied by 8, which first encoder pulse is counted by the pulse counter 93.

The above comparison circuit 95, in the reference embodiment, compares the value of the target signal generated by the target signal generating circuit 91 and the number of the 4-multiplied encoder pulse counted by the pulse counter 93 at every sampling period of 10 ms and outputs the difference thereof.

The above PI arithmetic circuitry 97 carries out the proportional operation (i.e. P operation), which generates the motor rotation control signal modulated (i.e. PMW modulation) with a pulse width proportional to the above difference, and the integral operation (i.e. I operation) which removes a residual deviation from the motor rotation control signal.

The above motor driving circuit 99 drives the DC brushless motor 51 according to the motor rotation control signal having removed of the above residual deviation by the PI arithmetic circuitry 97.

The above control unit 9 controls, in an earlier stage, the PI arithmetic circuitry 97 to generate the motor rotation control signal to be modulated with the pulse width corresponding to the target value of the target signal generated by the target signal generating circuit 91, and the motor driving circuit 99 drives the DC brushless motor 51 with the motor rotation control signal.

However, since the encoder pulse with the pulse number corresponding to the rotation number of the output shaft of the DC brushless motor 51 having started rotating, the operation of the control unit 9 changes as follows.

That is, the control unit 9 compares, by means of the comparison circuit 95, the value of the target signal generated by the target signal generating circuit 91 and the number of the 4-multiplied encoder pulse counted by the pulse counter 93 at every sampling period of 10 ms so as to output the difference thereof and, by means of the PI arithmetic circuitry 97, generate the motor rotation control signal modulated with the pulse width not corresponding to the target value of the target signal but proportional to the difference having got by the comparison circuit 95. And, the control unit 9 drives the DC brushless motor 51 with the motor rotation control signal by means of the motor driving circuit 99.

Here, for example, when 0.06 l/h (little/hour) is set as the basic flow rate by means of the basic data setting-inputting portion 7a of the controller 7, the target value of the target signal generated by the target signal generating circuit 91 is determined as follows when the other basic data such as the inside diameter of the flexible tube 3 to be set by the basic data setting-inputting portion 7a have been determined.

First, in the reference embodiment, if the roller pump 5 transfers 8 ml of the liquid in the flexible tube 3 while the disc 5b makes 5 rotations, the disc 5b shall make 10*(60/8)=75 rotations in order to transfer 0.06 l/h of the liquid in the flexible tube 3.

And, because the disc 5b rotates by only 1/60 of the output shaft of the DC brushless motor 51 due to the reduction by the gear head 55, the output shaft of the DC brushless motor 51 shall make 75*60=4500 rotations in order to make the disc 5b75 rotations.

As above, the output shaft of the DC brushless motor 51 shall make 4500 revolutions/hour (rpm) in order to transfer 0.06 l/h of the liquid in the flexible tube 3. In this case, the encoder pulse of 500*4500=2.25*10^6 (^; the power) pulses/hour is output from the encoder unit 53, and this encoder pulses are multiplied by 4 by the frequency 4-multiplying circuit 93a Therefore, the pulse number of the 4-multiplied encoder pulse to be counted by the pulse counter 93 shall be 4*2.25*10^6=9*10^6 per hour. And then, the pulse counter 93 counts 9*10^6÷(60*60*10^2)=25 pulses of the 4-multiplied encoder pulse every sampling period of 10 ms. As a result, the target signal generating circuit 91 decides the target value of the target signal to be 25.

That is, the target value of the target signal generated by the target signal generating circuit 91 becomes the pulse number of the 4-multiplied encoder pulse to be counted by the pulse counter 93 every sampling period of 10 ms when the liquid with the basic flow rate having been set by the basic data setting-inputting portion 7a of the controller 7 is transferred in the flexible tube 3 for an hour.

Next, in the liquid transferring pump system 1 of the reference embodiment, especially the drive of the roller pump 5 by the DC brushless motor 51 is described.

In transferring the liquid in the flexible tube 3 with the liquid transferring pump system 1 of the reference embodiment, the flexible tube 3 is put between the supporting plate 5e and the free rollers 5d of the roller pump 5. And, the controller 7 is power-fed, and the required data for the operation of the roller pump 5 are input-set as the basic data from the basic data setting-inputting portion 7a of the controller 7. The basic data contains the inside diameter of the flexible tube 3, the basic flow rate of the liquid in the flexible tube 3 and operation time of the roller pump 5.

Then, the target signal is generated on the basis of the basic data by the target signal generating circuit 91, the motor rotation control signal of the pulse. width corresponding to the target value of the target signal is generated by the PI arithmetic circuitry 97, and the DC brushless motor 51 of the roller pump 5 is driven by means of the motor driving circuit 99 with the rotation speed according to the basic flow rate of the liquid in the flexible tube 3.

With the drive of the DC brushless motor 51, the rotation of the output shaft cf the DC brushless motor 51 is transmitted to the disc 5b through the gear head 55 and the driving shaft 5a, and the disc 5b rotates with the rotation speed of 1/60 of the output shaft of the DC brushless motor 51, whereby the liquid in the flexible tube 3 is transferred from one end side toward the other end side.

And, with the drive of the DC brushless motor 51, the encoder pulse is output from the encoder unit 53 having the base plate 53a on the output shaft of the DC brushless motor 51, and the 4-multiplied encoder pulse with the pulse number being got by multiplying the number of the encoder pulse by 4 by means of the frequency 4-multiplying circuit 93a is counted by the pulse counter 93.

And, the comparison between the target value of the target signal and the pulse number of the 4-multiplied encoder pulse counted by the pulse counter 93 is carried out by the comparison circuit 95 every sampling period of 10 ms. If there exists a difference therebetween, the motor rotation control signal for eliminating the difference is generated by the PI arithmetic circuitry 97, whereby the rotation speed of the DC brushless motor 51 to be driven by the motor driving circuit 99 is changed by the motor rotation control signal.

As a result, the rotation speed of the DC brushless motor 51 converges so that the liquid of the basic flow rate is transferred in the flexible tube 3.

In such a serial operation, the liquid transferring pump system 1 of the reference embodiment has the following features in recognizing the liquid flow rate, in the flexible tube 3, required for carrying out so-called feedback control of the DC brushless motor 51 by means of the pulse signal generated according to the rotation speed of the output shaft of the DC brushless motor 51.

First, since the pulse counter 93 of the control unit 9 counts the pulse number of the 4-multiplied encoder pulse to be obtained by multiplying the encoder pulse to be output from the encoder unit 53 by 4 by means of the frequency 4-multiplying circuit 93a, the resolution of the liquid flow rate becomes 4 times in comparison with the case of directly counting the encoder pulse itself to be output by the encoder unit 53 by means of the pulse counter 93.

Besides, since the encoder unit 53 of the motor unit 50 consists of the first and second phase encoders so that the first and second encoder pulses are output from the respective encoders with shifting the phases by half the period each other, the resolution of detecting the rotation of the output shaft of the DC brushless motor 51 becomes 2 times in comparison with using a single phase encoder. Further, since the disc 5b which pivotally-supports the free roller 5d of the roller pump 5 used to transfer the liquid in the flexible tube 3 is connected through the gear head 55 to the output shaft of the DC brushless motor 51 in order to reduce the rotation of the disc 5b to 1/60 of that of the output shaft of the DC brushless motor 51, the resolution of the liquid flow rate in the flexible tube 3 to be detected with the encoder pulse to be output by the encoder unit 53 becomes 60 times in comparison with the case of rotating the disc 5b directly with the output shaft of the DC brushless motor 51.

Accordingly, in the reference embodiment, the resolution of the liquid flow rate to be detected with the encoder pulse to be output by the encoder unit 53 becomes 2*60*4=480 times in comparison with the case wherein the encoder unit 53 is formed by a single phase encoder, the disc 5b of the roller pump 5 is connected directly with the output shaft of the DC brushless motor 51, and the pulse counter 93 just counts the encoder pulse to be output by the encoder unit 53 without multiplying it by 4 (hereinafter, assumed structure).

Therefore, if the rotation speed of motor in the reference embodiment and in the assumed structure is the same, the accuracy of so-called feedback control of the DC brushless motor 51 by means of the control unit 9 in the reference embodiment is 480 times of that of the assumed structure.

In other words, in the liquid transferring pump system 1 of the reference embodiment, even if the rotation speed of the DC brushless motor 51 is reduced to 1/480 of that of the above assumed structure, the accuracy of the feedback control of the control unit 9 can be maintained to be the same as that of the assumed structure.

The above is the operation of the liquid transferring pump system in accordance with the reference embodiment of the present invention.

In this way, according to the liquid transferring pump system 1 of the reference embodiment, when the control unit 9 feedback-controls the DC brushless motor 51 of the roller pump 5 to be driven for transferring the liquid in the flexible tube 3 by using the pulse number of the encoder pulse from the encoder unit 53, the pulse number of the 4-multiplied encoder pulse, which is obtained by multiplying the pulse number of the encoder pulse by 4 by means of the frequency 4-multiplying circuit 93a, is counted by means of the pulse counter 93.

Therefore, since the encoder unit 53 can multiply the pulse number of the encoder pulse which corresponds to the rotation of the output shaft of the DC brushless motor 51, the liquid in the flexible tube 3 can be transferred with high constantivity even if the light-passing portion 53e and the light-interrupting portion 53f of the first and second encoding patterns 53c, 53d can not been increased due to structural limitation. That is, since the resolution of the liquid flow rate to be detected with the encoder pulse to be output by the encoder unit 53 is enhanced, the number of rotation of the output shaft of the DC brushless motor 51 can be detected with sufficiently high resolution even if the rotation speed of the output shaft of the DC brushless motor 51 are lowered.

Next, a liquid transferring pump system in accordance with the embodiment of the present invention is described.

Here, a roller pump 5 and a controller 7, which constitute the liquid transferring pump system of the present embodiment along with a later-described control unit 9A, are the same as the roller pump 5 and the controller 7 of the reference embodiment, respectively. Therefore, description about the structure of the roller pump 5 and the controller 7 of the present embodiment will be omitted.

Also, in the liquid transferring pump system 1 of the present embodiment, the first photo-interrupter 53g generates 250 pulses of the first encoder pulse per one rotation of the output shaft of the DC brushless motor 51 similarly to the liquid transferring pump system 1 of the reference embodiment.

Further, in the liquid transferring pump system 1 of the present embodiment, the second photo-interrupter 53h generates 250 pulses of the second encoder pulse per one rotation of the output shaft of the DC brushless motor 51 similarly to the liquid transferring pump system 1 of the reference embodiment.

Still further, in the liquid transferring pump system 1 of the present embodiment, the encoder unit 53 outputs 500 pulses of the encoder pulse, which is composed of the first and second encoder pulses, per one rotation of the output shaft of the DC brushless motor 51 similarly to the liquid transferring pump system 1 of the reference embodiment.

Besides, in the liquid transferring pump system 1 of the present embodiment, the first phase encoder corresponding to the sub-encoder in the claim can be formed of the first encoding pattern 53c and the first photo-interrupter 53g and similarly the second phase encoder corresponding to the sub-encoder in the claim can be formed of the second encoding pattern 53d and the second photo-interrupter 53h, similarly to the liquid transferring pump system 1 of the reference embodiment.

Figure 6:
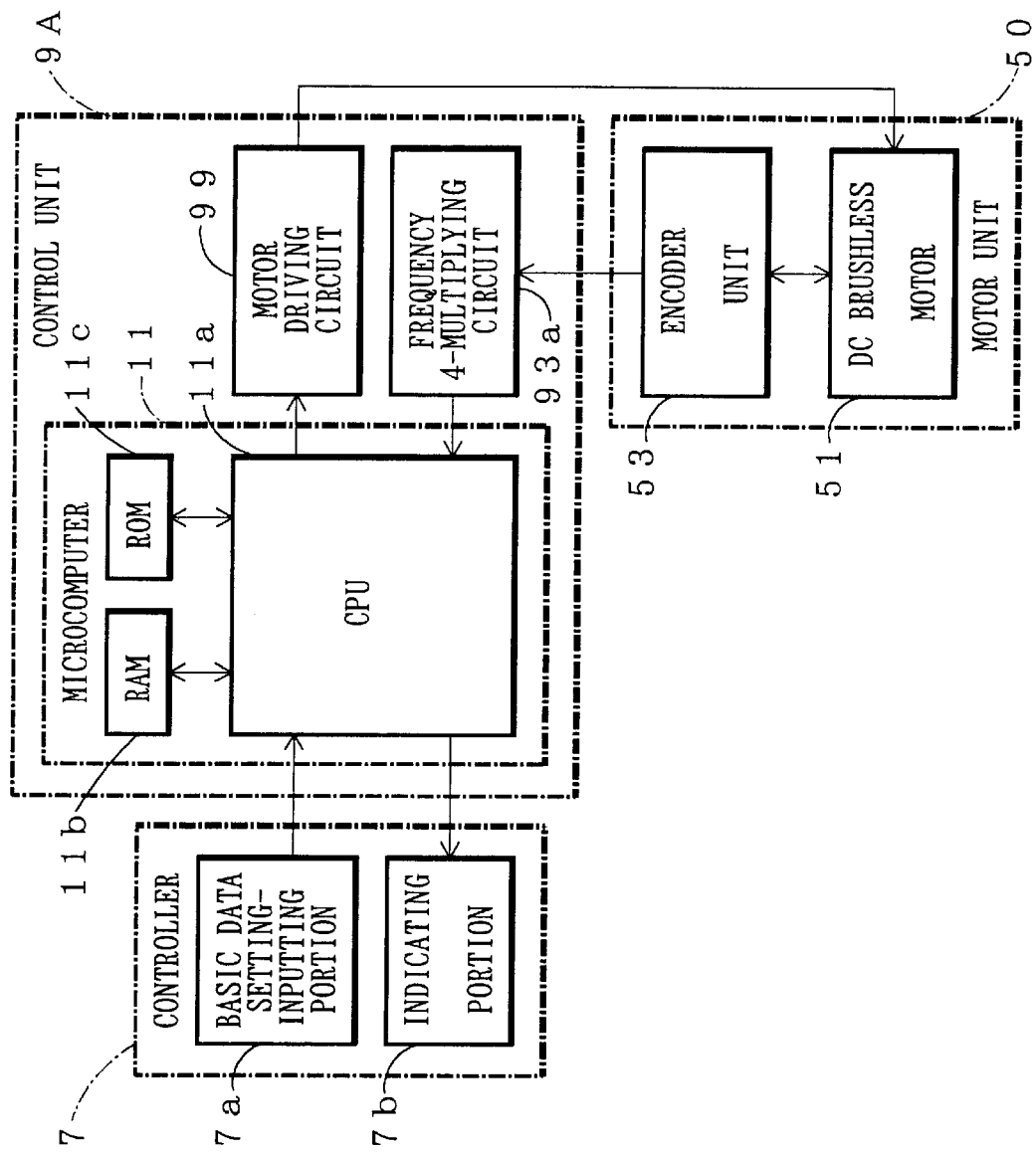
FIG. 6 is a block diagram showing an electrical structure of a control unit to control the drive of the roller pump of FIG. 2 in a embodiment of the liquid transferring pump system in accordance with the present invention.

And, as shown in FIG. 6, the control unit 9A of the present embodiment has a microcomputer 11 instead of the target signal generating circuit 91, the pulse counter 93 except the frequency 4-multiplying circuit 93a, the comparison circuit 95, and the PI arithmetic circuitry 97, which are included in the control unit 9 of the reference embodiment shown in FIG. 5.

The above microcomputer 11 is formed of CPU 11a, RAM 11b and ROM 11c. The basic data setting-inputting portion 7a of the controller 7, the indicating portion 7b and the motor driving circuit 99 are connected to the above CPU 11a. And, the encoder unit 53 of the motor unit 50 is also connected to the CPU 11a through the frequency 4-multiplying circuit 93a.

And, the data area and the work area to be used for various processing work are provided on the above RAM 11b. Areas to be used for various flags and buffer are provided on the work area. The control program to make CPU 11a carry out various processing operation is stored in the above ROM 11c.

And, in the control unit 9A of the liquid transferring pump system of the present embodiment, the 4-multiplied encoder pulse from the frequency 4-multiplying circuit 93a is counted by the processing which CPU 11a carries out according to the control program stored in the above ROM 11c, and the count value is stored as the pulse count value Cb in the pulse count area of RAM 11b.

Next, the processing which CPU 11a carries out according to the control program stored in the above ROM 11c is described referring to the flowcharts of FIGS. 7–10.

The microcomputer 11 starts by receiving the power feeding from a non-illustrated battery by switching a non-illustrated power switch ON and the program starts. At first, the CPU 11a carries out the initial setting to zero-reset the count value of various counter areas of RAM 11b and the timer value of the timer area, as shown in FIG. 7 (Step S1).

After the initial setting of Step S1, whether or not the basic data have been input set is checked (Step S3), and if not input-set (Step S3, N), Step S3 is repeated until the basic data are input-set.

On the other hand, when the basic data have been input-set (Step S3, Y), the pulse value of the motor rotation control signal to be output to the motor driving circuit 99 is calculated in order to control the rotation of the output shaft of the DC brushless motor 51 on the basis of the basic data, and the integer -portion of the calculated value is set as the target pulse value Pa (Step S5). Next, the target value switching timer value Ta is calculated on the basis of the decimal portion of the target pulse value Pa (Step S7), and the flow returns to Step S3.

Figure 7:
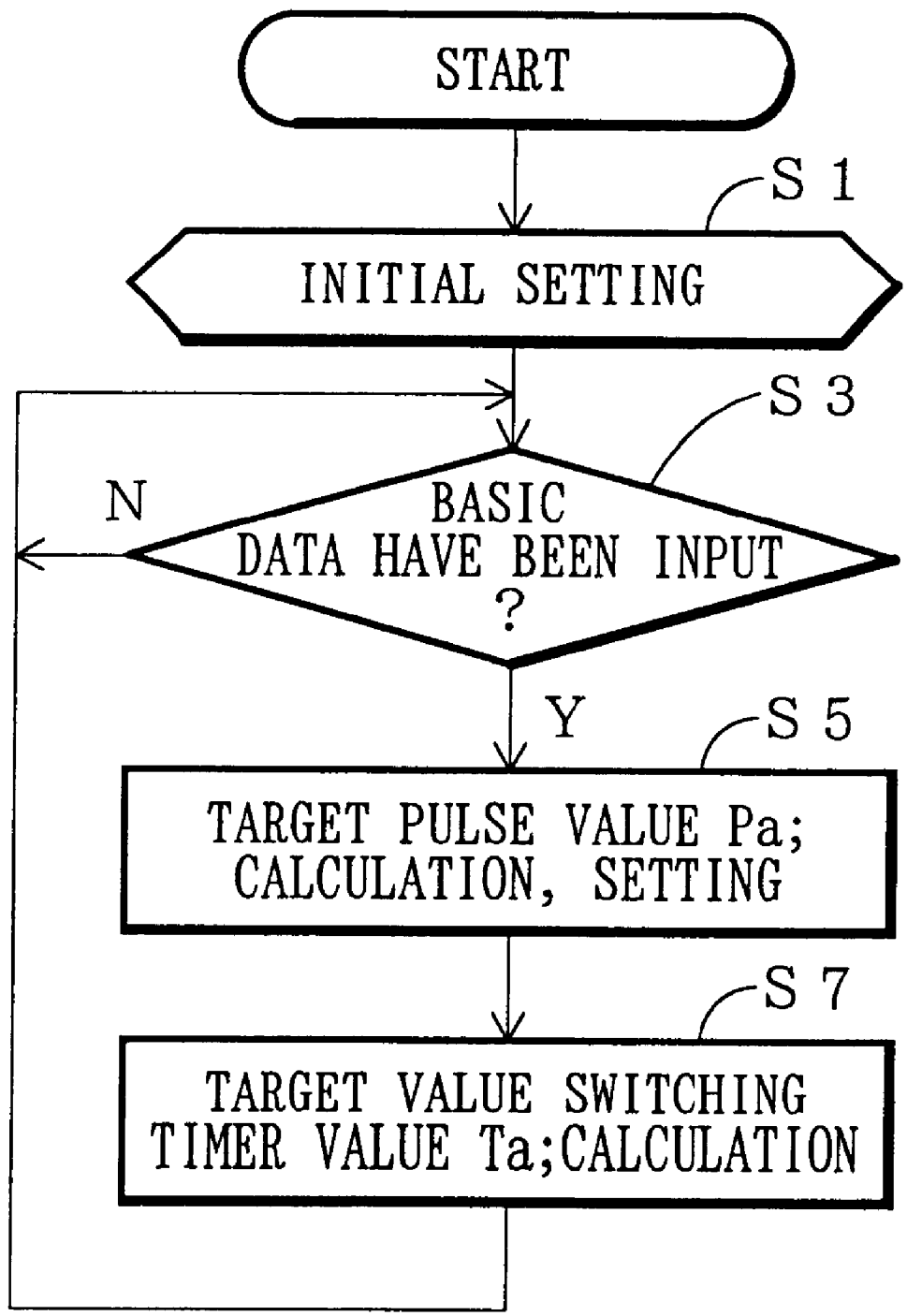
FIG. 7 is a flowchart of a main routine showing a processing to be carried out by a CPU according to a control program stored in a ROM of FIG. 6.
Figure 8:
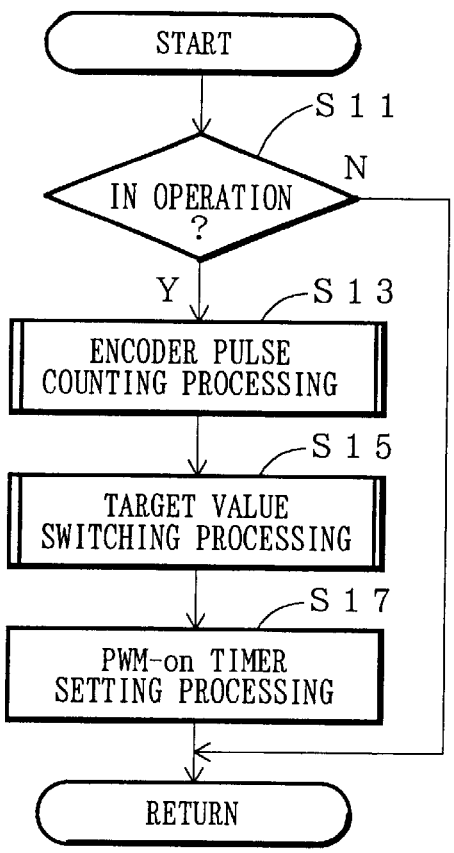
FIG. 8 is a flowchart of a subroutine showing a target value calculating processing of FIG. 7.

And, the CPU 11a executes the interrupt handling shown in the flowchart of FIG. 8 according to the control program stored in ROM 11c by interrupting into the main routine of FIG. 7 in every 10 ms after having checked the input-setting of the basic data of Step S3.

In the interrupt handling of FIG. 8, at first, whether or not the roller pump 5 is in operation by the rotation of the DC brushless motor 51 (Step S11). The interrupt handling ends and the control returns to the main routine of FIG. 7 when not in operation (Step S11, N), and the encoder pulse counting processing is carried out (Step S13) when in operation (Step S11, Y). Following the above, the CPU 11a executes the target value switching processing (Step S15) and the PWM-on timer setting processing (Step S17) successively and finishes the interrupt handling, and then the control returns to the main routine of FIG. 7.

Figure 9:
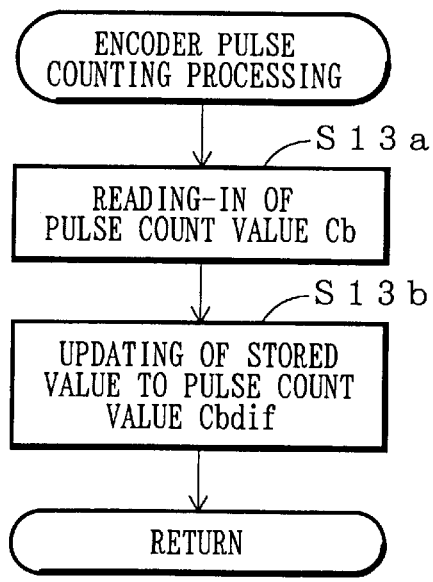
FIG. 9 is a flowchart of a subroutine showing a drive processing of FIG.7.

And as shown in FIG. 9, in the encoder pulse counting processing of Step S13, at first the pulse count value Cb stored in the pulse count area of RAM 11b is read-in (Step S13a), and next the previous pulse count value Cb having been read-in in the previous Step S13a is subtracted from the present pulse count value Cb. The stored value in the rotation number buffer area of RAM 11b is updated with the pulse count value Cbdif which has been obtained by the above subtraction (Step S13b), the encoder pulse counting processing ends, and the control proceeds to Step S15 of FIG. 8.

Figure 10:
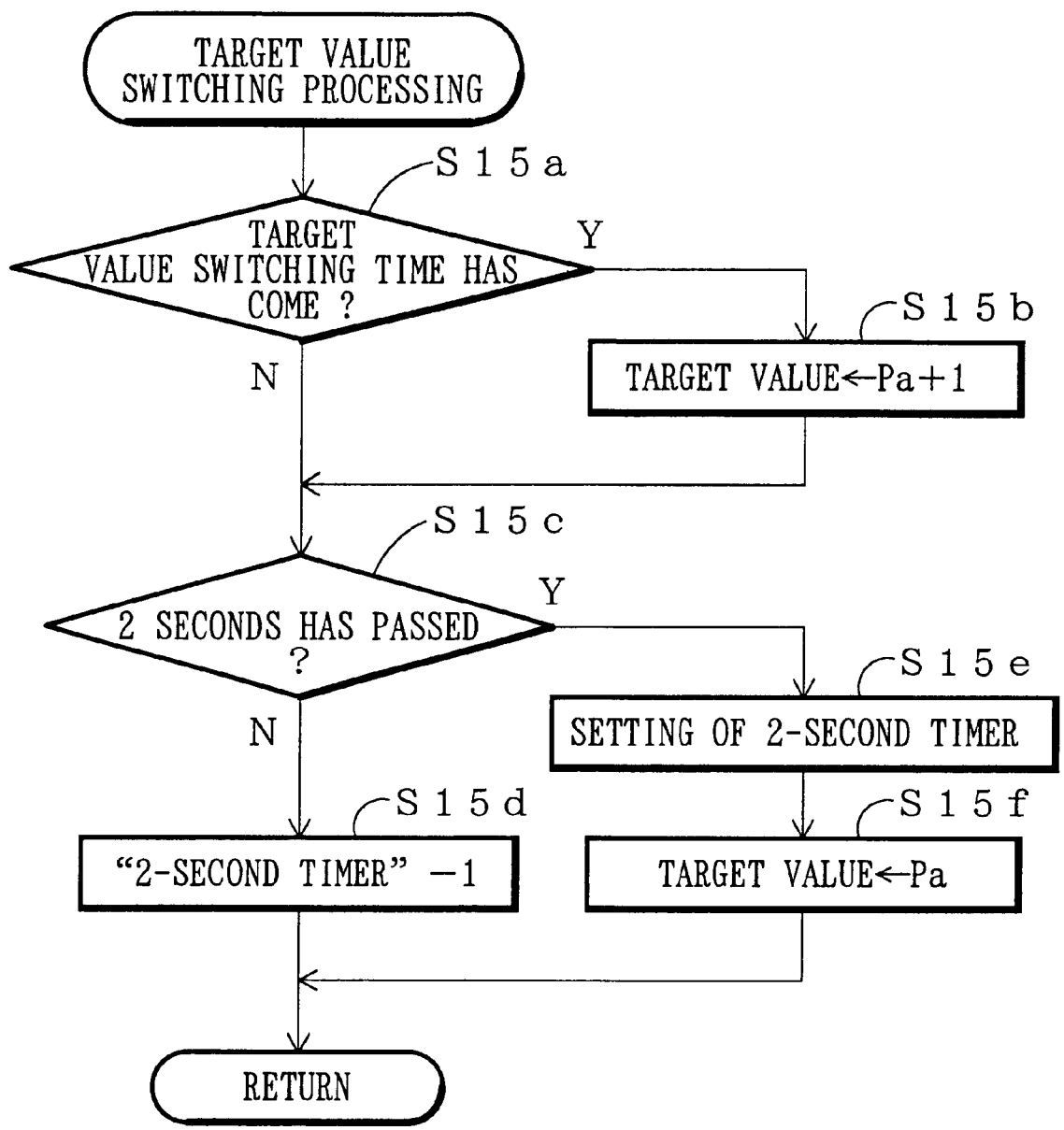
FIG. 10 is a flowchart of a subroutine showing a drive processing of FIG. 7.

And as shown in FIG. 10, in the target value switching processing of Step S15, at first the remaining time counted value in the 2-second timer counter area of the RAM 11b has reached the target value switching timer value Ta having calculated in Step S7 is checked, that is, whether or not the target value switching time has come is checked (Step S15a). Then, is case of "no" (Step S15a, N) the control goes to a later-described Step S15c, and in case of "yes" (Step S15a, Y) the control goes to Step S15c after having set the value of "Pa (calculated in Step S5 )+1" as the target value (Step S15b).

In Step S15c, whether or nor the remaining time counted value of the 2-second timer has reached "0", that is, 2 seconds has passed, is checked. If not (Step S15c, N), "1" is subtracted from the remaining time counted value of the 2-second timer (Step S15d), the target value switching processing ends, and the control goes to Step S17 of FIG. 8.

On the other hand, when 2 seconds has passed (Step S15c, Y), the remaining time count is started by the 2-second timer, that is, the 2-second timer is set (Step S15e), the target pulse value Pa having been set in Step S5 is set as the target value (Step S15f), the target value switching processing ends, and the control goes to Step S17 of FIG. 8.

Further, in the PWM-on timer setting processing of Step S17, a time length of pulse-ON level (i.e. PWM-on time) of the motor rotation control signal having a fixed pulse period is set as a PWM-on timer time in order to set the duty ratio of the motor rotation control signal according to the new target value having set in Step S15b or Step S15f, and the interrupt handling ends, thereby returning to the main routine of FIG. 7.

As understood with the above, in the present embodiment, the processing in Step S5 in the flowchart of FIG. 7 corresponds to the desirable drive pulse calculating means and the integer judging means in the claim. And, the processing in Step S15b in the flowchart of FIG. 10 corresponds to the approximate pulse calculating means in the claim. Also, the processing in Step S7 in FIG. 7 corresponds to the period calculating means in the claim.

That is, in Step S7 in FIG. 7, only the calculation of the target value switching timer value Ta corresponding to either one of the first period time and the second period time in the claim is executed on the basis of the decimal portion of the target pulse value Pa.

However, the time, which has passed until recognizing that 2 seconds has passed in Step S15c after the value of "Pa (calculated in Step S5)+1" has set as the target value in Step S15b after confirmation of having reached the target value switching time in Step S15a of FIG. 10, corresponds to the other of the first period time and the second period time in the claim That is, the above is equivalent to a state that the first period time and the second period time are both calculated in Step S7 in FIG. 7, and the processing of Step S7 corresponds to the period calculating means in the claim.

And, the processing of Steps S5,S7 in FIG.7 and Step S15b in FIG. 10 corresponds to the drive frequency adjusting means in the claim.

Next the driving-control operation ofthe DC brushless motor 51 by the microcomputer 11 of the control unit 9A in the liquid transferring pump system 1 of the present embodiment is described.

In the liquid transferring pump system 1 of the present embodiment, at first the flexible tube 3 is set in the roller pump 5 for transferring the liquid in the flexible tube 3, similarly to the liquid transferring pump system 1 ofthe reference embodiment. The basic data are input-set from the basic data setting-inputting portion 7a of the controller 7, and then the following processing operation is carried out by the microcomputer 11.

That is, the target value Ca is decided on the basis of the basic data, the motor rotation control signal with the pulse width corresponding to the target value Ca is output by the motor driving circuit 99, and the DC brushless motor 51 of the roller pump 5 is driven with the rotation speed according to the basic flow rate of the liquid in the flexible tube 3 having been input-set by the controller 7.

On driving the DC brushless motor 51, the encoder pulse from the encoder unit 53 is multiplied by 4 by means of the frequency 4-multiplying circuit 93 to produce the 4-multiplied encoder pulse. The pulse number of the 4-multiplied encoder pulse is counted, and the target pulse value Pa of the motor rotation control signal which is going to be output to the motor driving circuit 99 is calculated every sampling period of 10 ms, which target pulse value Pa is arranged to get rid of the difference between the above counted 4-multiplied encoder pulse and the target value Ca.

Here, when the roller pump 5 is to transfer 9.9 ml of the liquid in the flexible tube 3 while the disc 5b makes 10 rotations, the disc 5b shall make $10*(60/9.9) \approx 60.6$ rotations in order to transfer 0.06 l/h of the liquid in the flexible tube 3.

And, when the difference of the rotation number between the output shaft of the DC brushless motor 51 and the disc 5b due to the reduction by the gear head 55 is considered, the output shaft of the DC brushless motor 51 shall make $60.6*60=3,636$ rotations/hour in order to transfer 0.06 l/h of the liquid in the flexible tube 3. In this case, $500*3,636=1,818,000$ pulses/hour of the encoder pulse shall be output from the encoder unit 53.

Therefore, the counted number of the 4-multiplied encoder pulse shall be $4*1,818,000=7,272,000$ per hour, and accordingly $7,272,000/(60*60*10^2)=20.2$ pulses of the 4-multiplied encoder pulse shall be counted every sampling period of 10 ms, whereby the calculated target value Pa comes to "20.2".

Otherwise, when the roller pump 5 is to transfer 10.0 ml of the liquid in the flexible tube 3 while the disc 5b makes 10 rotations, the disc 5b shall make $10*(60/10)=60$ rotations in order to transfer 0.06 l/h of the liquid in the flexible tube 3.

And, when the difference of the rotation number between the output shaft of the DC brushless motor 51 and the disc 5b due to the reduction by the gear head 55 is considered, the output shaft of the DC brushless motor 51 shall make $60*60=3,600$ rotations/hour in order to transfer 0.06 l/h of the liquid in the flexible tube 3. In this case, $500*3,600=1.8*10^6$ pulses/hour of the encoder pulse shall be output from the encoder unit 53.

Therefore, the counted number of the 4-multiplied encoder pulse shall be $4*1.8*10^6=7.2*10^6$ per hour, and accordingly $7.2*10^6/(60*60*10^2)=20$ pulses of the 4-multiplied encoder pulse shall be counted every sampling period of 10 ms, whereby the calculated target value Pa comes to "20".

Like the above, the target pulse value Pa of the motor rotation control signal calculated every sampling period of 10 ms can be a mixed decimal or an integer.

And, if the calculated target pulse value Pa is an integer like the above "20", the motor rotation control signal with the pulse corresponding to the target pulse value Pa =20 is output to the motor driving circuit 99 during 2 seconds, i.e. 10 ms (sampling period)*200 (the maximum counted value Cc of the 2-second timer counter area).

On the other hand, when the target pulse value Pa is not an integer, an integer smaller than and nearest to the target pulse value Pa is set as the target pulse approximate value Pa', that is, if the target pulse value Pa is of the above "20.2" for example, "20" is set as the target pulse approximate value Pa'.

Here, there shall be (Pa'+1)*(2-Ta)+Pa'*Ta=2Pa, where, Pa=20.2, Pa'=20, and therefore Ta=1.6.

In this case, the motor rotation control signal with the pulse corresponding to the target pulse approximate value Pa'=20 is output to the motor driving circuit 99 during the period time Ta=1.6 seconds. Before or after the above, the motor rotation control signal with the pulse width corresponding to the pulse value="21", i.e. the target pulse approximate value Pa'+1, is output to the motor driving circuit 99 during 0.4 seconds, i.e. 2 seconds–Ta (i.e. 1.6 seconds)).

As a result, when the target pulse value Pa is not an integer, i.e. in case of "20.2" for example, the pulse number of the motor rotation control signal to be output to the motor driving circuit 99 during 1.6 seconds is 20*1.6*100=3,200, and the pulse number during 0.4 seconds is 21*0.4*100= 840, whereby the total during 2 seconds comes to 4,040 pulses. This total pulse number is the same as that of the case wherein the motor rotation control signal with the pulse corresponding to the target pulse value Pa=20.2 is output during 2 seconds, i.e. 20.2*2*100=4,040.

And, following the above, the target pulse value Pa is calculated every 2 seconds, the motor rotation control signal whose the pulse value per 10 ms is an integer is always output to the motor driving circuit 99 regardless of the target pulse value Pa being an integer.

Accordingly, the rotation speed of the DC brushless motor 51 driven through the motor driving circuit 99 is regulated by the motor rotation control signal according to the target pulse value Pa to be calculated with the period of 2 seconds.

As a result, the rotation speed of the DC brushless motor 51 converges to the speed of transferring the basic flow rate of the liquid in the flexible tube 3.

The above is the operation of the liquid transferring pump system in accordance with the embodiment of the present invention.

The effects similar to those of the liquid transferring pump system 1 of the reference embodiment can be attained with the above liquid transferring pump system 1 of the present embodiment.

Besides, according to the liquid transferring pump system 1 of the present embodiment, since the output control of the motor rotation control signal can be carried out by the data processing using only integer even if the target pulse value Pa is not an integer when the microcomputer 11 of the control unit 9A calculates the target pulse value Pa and the motor rotation control signal with the pulse width corresponding to the target pulse value Pa is output to the motor driving circuit 99, the output control of the motor rotation control signal can be carry out with a sufficient speed by use of CPU 11a which is not expensive and is designed only for the integral data processing.

Here, in the liquid transferring pump systems 1 of the present embodiment, the structure, wherein the encoder unit 53 has the first and second phase encoders so that the encoder unit 53 outputs the first and second encoder pulses, that is, outputs the encoder pulse with half the pulse period of the single phase encoder pulse, may be eliminated.

And, in the liquid transferring pump systems 1 of the present embodiment, the structure, wherein the disc 5b of the roller pump 5 rotates by ⅟₆₀ of the rotation of the output shaft of the DC brushless motor 51 by means of the reduction gear train in the gear head 55, may be eliminated independently or along with the above structure of the 2-phase encoder.

However, if the encoder unit 53 has the 2-phase encoder as in the liquid transferring pump systems 1 of the present embodiment, the pulse number of the encoder pulse to be output from the encoder unit 53 comes to twice the single phase one, and in case that the disc 5b of the roller pump 5 rotates only ⅟₆₀ of the rotation of the output shaft of the DC brushless motor 51, the pulse number of the encoder pulse form the encoder unit 53 per one rotation of the disc 5b comes to 60 times the disc 5b being directly rotated by the output shaft of the DC brushless motor 51.

Therefore, the resolution of the liquid flow rate detected by the pulse counter 93 with the pulse number of the encoder pulse is enhanced. And, as a result, even if the rotation speed of the output shaft of the DC brushless motor 51 is lowered, the rotation number of the output shaft of the DC brushless motor 51 can be detected with sufficiently high resolution, the liquid in the flexible tube 3 can be transferred with high constantivity.

Besides, if the encoder unit 53 is formed with the 2-phase encoder as in the first and liquid transferring pump systems 1 of the present embodiment, it is not necessary to increase the steps of the frequency 4-multiplying circuit 93a, which is formed of a multivibrator circuit for example, in order to increase the count number of the encoder pulse by means of the pulse counter 93, while preventing the pulse counter 93 from becoming complicated.

Here, the structure of the 2-phase encoder unit 53, wherein the first and second encoding patterns 53c,53d concentrically arranged on the base plate 53a are optically read by the first and second photo-interrupters 53g,53h in the present embodiment, is not limited thereto.

For example, a single encoding pattern provided on the base plate 53a may be optically read by a plurality of photo-interrupters arranged in a circumferential direction of the base plate 53a. Otherwise, a single encoding pattern provided on each of a plurality of circular base plates may be optically read by a respective photo-interrupter.

And, the encoder unit 53 may be of a multi-phase one, i.e. more than two (2) phase, not limited to the ones in the present embodiment. Also, the encoder unit 53 may be of a different type one such as a contact-slide type one using a conductive pattern and a brush, not limited to the photo-electric ones in the present embodiment.

Further, the reduction ratio of the rotation speed of the output shaft of the DC brushless motor 51 by the gear head 55 may be suitably changed, not limited to ⅟₆₀ in the present embodiment.

And, in the present embodiment the liquid transferring pump system, wherein the flexible tube 3 is put between the circumferential surfaces of the free rollers 5d of the disc 5b and the inside surface of the supporting plate 5e and the disc 5b is rotated by the DC brushless motor 51 so as to transfer the liquid in the flexible tube 3, is described. However, the structure of the pumping portion may be, for example, of a cylindrical member crossing at right angles to the flexible tube 3 instead of the free roller 5d of the above roller pump 5.

And, in the present embodiment, the pulse number to be output to the motor driving circuit 99 as the motor rotation control signal during the period time Ta or during the period of "2 seconds-the period time Ta" is set to the target pulse approximate value Pa' of integer which is smaller than and closest to the target pulse value Pa or to the value "Pa'+1" of integer which is smaller than and closest to the target pulse value Pa, wherein the difference therebetween is only "1".

Here, for example, when the target pulse value Pa is "20.2", the pulse number, based on "20" and "22" whose difference is "2", to be output to the motor driving circuit 99 as the motor rotation control signal may be used.

However, as in the present embodiment, the case, wherein the pulse number to be output to the motor driving circuit 99 as the motor rotation control signal based on the smaller difference, is advantageous in fewer occurrence of rotation speed fluctuation caused by the rotation speed difference of the output shaft of the DC brushless motor 51, which difference arises when the output pulse number is changed during the 2 seconds.

Further, though the DC brushless motor 51 is used as the drive source to transfer the liquid in the flexible tube 3 in the present embodiment, a motor other than the DC brushless motor may, of course, be used.

SUSCEPTIBILITY IN INDUSTRIAL APPLICATION

As is obvious from the present embodiment described above, according to the liquid transferring pump system of the present invention, even if the motor is rotated with low speed, high transferring constantivity can be attained because of the high resolution of the motor rotation number by increasing the pulse number per one rotation of the motor.

And, according to the liquid transferring pump system of the present invention, since the frequency of the multiplied rotation pulse signal is increased by largely increasing multiplying number of the frequency multiplying means also without causing large-sizing of the structure, further high transferring constantivity can be attained because of the further high resolution of the motor rotation number.

Further, according to the liquid transferring pump system of the present invention, since the number of the sensor to detect the encoding pattern of the base plate is m in accordance with the number of the sub-encoder, the subrotation pulse signal can be generated by m according to the output from each sensor.

And, according to the liquid transferring pump system of the present invention, the structure of the encoder can be simplified in comparison with the structure wherein one encoding pattern is provided on each of the base plates, thereby downsizing the whole liquid transferring pump system.

Further, according to the liquid transferring pump system of the present invention, since the movement of the movable squeezing member per rotation of the motor is small due to the reduction mechanism, in other words, the rotation number of the motor per movement of the movable squeezing member is large due to the reduction mechanism and therefore the pulse number of the rotation pulse signal to be output by the encoder increases, even if the motor is rotated with low speed, high transferring constantivity can be securely attained because of the high resolution of the motor rotation number with the rotation pulse signal.

And, according to the liquid transferring pump system of the present invention, since the output control of the motor rotation control signal can be carried out by the data processing using only integer even if the target pulse value Pa is not an integer when the microcomputer of the control unit calculates the target pulse value Pa and the motor rotation control signal with the pulse width corresponding to the target pulse value Pa is output to the motor driving circuit, the output control of the motor rotation control signal can be carry out with a sufficient speed by use of CPU which is not expensive and is designed only for the integral data processing.

Further, according to the liquid transferring pump system of the present invention, the difference of the first and second approximate pulse numbers is the smallest, occurrence of rotation speed fluctuation can be prevented by decreasing the rotation speed difference of motor when a state of the first approximate pulse number being output switches to another state of the second approximate pulse number being output or viceversa.

What is claimed is:

1. A liquid transferring pump system, wherein a motor for moving a movable squeezing member, which squeezes a flexible tube so as to transfer a liquid therein from an upstream side toward an downstream side thereof, is driven according to a drive pulse signal having a frequency determined correspondingly to a target flow rate of the liquid in the tube, and the frequency of the drive pulse signal is increased and decreased according to the frequency determined correspondingly to the target flow rate on a basis of the frequency of the drive pulse signal and a frequency of a rotation pulse signal which is output by an encoder correspondingly to rotation number of the motor so that a flow rate of the liquid in the tube agrees with the target flow rate, and wherein a frequency multiplying means to receive the rotation pulse signal to be output by the encoder and then to output a multiplied pulse signal to be obtained by multiplying the frequency of the rotation pulse signal by n and a drive frequency adjusting means to increase and decrease the frequency of the drive pulse signal according to the frequency determined correspondingly to the target flow rate so that a frequency of the multiplied pulse signal converges in the frequency determined correspondingly to the target flow rate are provided, the drive frequency adjusting means having a desirable drive pulse calculating means that calculates pulse number, per unit time, of an ideal drive pulse signal for converging the frequency of the multiplied pulse signal in the frequency determined correspondingly to the target flow rate at every determined time period when the frequency of the multiplied pulse signal is calculated based on sampling number of the multiplied pulse signal, an integer judging means that judges whether or not the pulse number, per the unit time, of the ideal drive pulse signal is integer, an approximate pulse calculating means that calculates a first approximate pulse number and a second approximate pulse number, which are two integers smaller and larger, respectively, than the pulse number, per the unit time, of the ideal drive pulse signal, when the integer judging means has judged that the pulse number, per the unit time, of the ideal drive pulse signal is not integer, and a period calculating means that calculates the first period time and the second period time wherein a total of a first value of multiplying the first approximate pulse number by the first period time and a second value of multiplying the second approximate pulse number by the second period time is equal to a value of multiplying the pulse number, per the unit time, of the ideal drive pulse signal by the unit time and also another total of the first period time and the second period time is equal to the unit time, wherein, when the integer judging means has judged that the pulse number, per the unit time, of the ideal drive pulse signal is not integer, increase and decrease of the frequency of the drive pulse signal according to the frequency determined correspondingly to the target flow rate is carried out by means of successively executing a pulse signal output of the first approximate pulse number over the first period time and a pulse signal output of the second approximate pulse number over the second period time.

2. The liquid transferring pump system as set forth in claim 1, wherein the approximate pulse calculating means calculates two integers smaller and larger, respectively, than and closest to the pulse number, per the unit time, of the ideal drive pulse signal as the first approximate pulse number and the second approximate pulse number.

3. The liquid transferring pump system as set forth in claim 1, wherein the encoder consists of m sets of sub-encoders which output subrotation pulse signals, which have determined frequency corresponding to the rotation number of the motor, with shifting phase by 1/m period, and by means of m subrotation pulse signals to be output by the m sets of sub-encoders a m-multiplied pulse signal to be obtained by multiplying the determined frequency by m is input into the frequency multiplying means as the rotation pulse signal to be output from the encoder and a m*n-multiplied pulse signal to be obtained by multiplying the determined frequency by m*n is output from the frequency multiplying means as the multiplied pulse signal.

4. The liquid transferring pump system as set forth in claim 3, wherein the encoder has a single base plate common to the sub-encoders, encoding patterns provided on the base plate correspondingly to the respective sub-encoders, and m sensors to detect the respective encoding patterns.

5. The liquid transferring pump system as set forth in claim 4, wherein one of the encoding patterns provided the base plate is common to the sub-encoders, and the sensors are arranged with a space in an extending direction of the one of the encoding patterns, whereby the one of the encoding patterns are detected by the sensors in different timing.

6. The liquid transferring pump system as set forth in claim 1, wherein a speed reduction mechanism is provided between the motor and the movable squeezing member.

7. The liquid transferring pump system as set forth in claim 2, wherein the encoder consists of m sets of sub-encoders which output subrotation pulse signals, which have determined frequency corresponding to the rotation number of the motor, with shifting phase by 1/m period, and by means of m subrotation pulse signals to be output by the m sets of sub-encoders a m-multiplied pulse signal to be obtained by multiplying the determined frequency by m is input into the frequency multiplying means as the rotation pulse signal to be output from the encoder and a m*n-multiplied pulse signal to be obtained by multiplying the determined frequency by m*n is output from the frequency multiplying means as the multiplied pulse signal.

8. The liquid transferring pump system as set forth in claim 6, wherein the encoder has a single base plate common to the sub-encoders, encoding patterns provided on the base plate correspondingly to the respective sub-encoders, and m sensors to detect the respective encoding patterns.

9. The liquid transferring pump system as set forth in claim 1, wherein a speed reduction mechanism is provided between the motor and the movable squeezing member.

* * * * *

UNITED STATES PATENT AND TRADEMARK OFFICE
CERTIFICATE OF CORRECTION

PATENT NO. : 6,299,600 B1 Page 1 of 1
DATED : October 9, 2001
INVENTOR(S) : Katsunori Masaoka et al.

It is certified that error appears in the above-identified patent and that said Letters Patent is hereby corrected as shown below:

<u>Title page,</u>
Item [22], please amend the PCT filing date to read -- July 1, 1999 --

Signed and Sealed this

Sixth Day of August, 2002

Attest:

JAMES E. ROGAN
Attesting Officer        *Director of the United States Patent and Trademark Office*